(12) United States Patent
Maingault et al.

(10) Patent No.: US 6,900,188 B2
(45) Date of Patent: May 31, 2005

(54) SYSTEM FOR TREATING WOUNDS AND METHOD FOR PRODUCING THIS SYSTEM

(75) Inventors: Philippe Maingault, Nanterre (FR);
Edit Dellacherie, Malzeville (FR);
Patrick Hubert, Nancy (FR);
Marie-Christine Houzelle, Vigy (FR);
Sophie Pelletier, Liffol le Grand (FR)

(73) Assignee: Les Laboratories Brothier (FR)

( * ) Notice: Subject to any disclaimer, the term of this patent is extended or adjusted under 35 U.S.C. 154(b) by 0 days.

(21) Appl. No.: 09/364,908

(22) Filed: Jul. 27, 1999

(65) Prior Publication Data

US 2001/0051149 A1 Dec. 13, 2001

(30) Foreign Application Priority Data

Jul. 31, 1998 (FR) .............................. 98 09858

(51) Int. Cl.$^7$ .................. A61K 31/734; A61K 31/7024
(52) U.S. Cl. ........................ 514/54; 514/23; 514/912; 424/429; 424/488; 424/499
(58) Field of Search ............................ 514/23, 54, 912, 514/26; 424/429, 488, 499; 536/119, 18.7, 3, 124, 115; 623/6.56

(56) References Cited

U.S. PATENT DOCUMENTS 5,336,668 A * 8/1994 della Valle et al. ........... 514/23

FOREIGN PATENT DOCUMENTS

| EP | 0 386 960 | | 9/1990 |
| EP | 0 724 888 A | | 8/1996 |
| WO | 9637519 | * | 11/1996 |

* cited by examiner

Primary Examiner—Jean C. Witz
(74) Attorney, Agent, or Firm—Greenberg Traurig LLP; Eugene C. Rzucidlo

(57) ABSTRACT

The wound-treatment system is natural and is adapted to change state in a reversible manner by passing from the gel state to the solution state and vice-versa, and has polysaccharide macromolecules (10, 20, 30) and aliphatic chains (11–15, 21–24, 31–33) attached to a single polysaccharide macromolecule. The aliphatic chains (21–24) attached to a polysaccharide macromolecule (20) are, in the gel state, associated with aliphatic chains (11, 12/13, 31) attached to at least one other polysaccharide macromolecule (10, 30) by physical bonds.

5 Claims, 2 Drawing Sheets

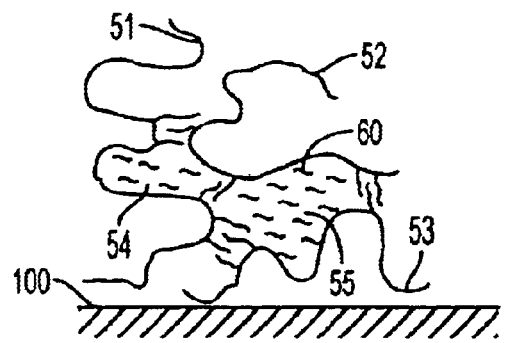
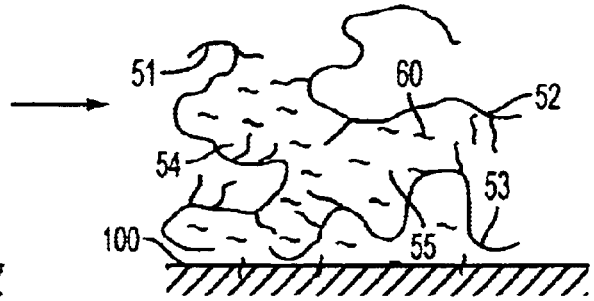
FIG. 3　　　　　　　　FIG. 4
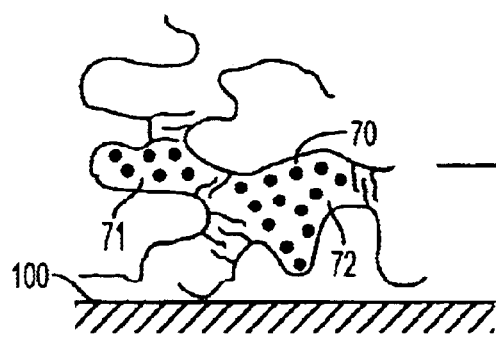
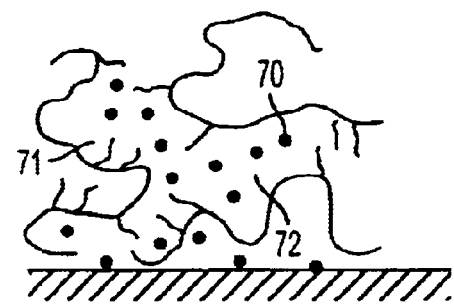
FIG. 5　　　　　　　　FIG. 6

SYSTEM FOR TREATING WOUNDS AND METHOD FOR PRODUCING THIS SYSTEM

The invention relates to a treatment product or system intended for the care of patches of necrosis, acute surgical wounds and other types of wounds.

Two types of wound-treatment products will mainly be considered.

The products of the first type are natural products and include polysaccharide molecules. They are, for example, alginate-based products. The products of this type have intrinsic natural properties which are highly effective in treating wounds.

The products of the second type are synthetic and for this reason have less effective curative properties.

The treatment products, whether natural or synthetic, are generally used as a solution or as a gel.

In the solution state the treatment product is easily applied and distributed over the wound and comes into close contact therewith. However, the distribution of the solution is generally not uniform and the solution inevitably runs out of the wound even with a protective, sealing dressing.

In the gel state the treatment product can certainly be held more easily on the wound by a dressing but does not come into close contact with it.

Reversible synthetic treatment gels are also known. These gels are known as "reversible" by reason of the fact that they can change state in a reversible manner by passing from the gel state to the solution state and vice-versa. This gel/solution reversibility is made possible by synthetic macromolecules forming the product, which have intrinsically reversible configurations.

Such reversibility is of great interest for the treatment of wounds. Indeed, in makes it possible, in particular, to apply the treatment product to a wound in the liquid state so that it spreads over the wound, conforms to the shape of it and comes into close contact with it. After a setting time the product gels and adheres to the wound without running.

Moreover, the gel close to the wound can liquify, particularly under the effect of temperature. In this way the product constantly remains in close contact with the wound even when the patient moves or the wound undergoes changes.

The invention aims to offer a reversible treatment product having properties even better than those of known reversible treatment products.

To this end the invention relates to a natural wound-treatment system, adapted to change state in a reversible manner by passing from the gel state to the solution state and vice-versa, having polysaccharide macromolecules and aliphatic chains attached to a single polysaccharide macromolecule.

The treatment system of the invention is not only reversible but also has highly effective intrinsic natural curative properties.

Moreover, the treatment system has the intrinsic properties of the aliphatic chains, which are of particular interest for the treatment of wounds and vary depending on the length of the aliphatic chain.

By way of example, the treatment products having aliphatic chains with eight carbon atoms have the property of inhibiting the division of microorganisms by "membrane permeation" to use the vocabulary of the person skilled in the art.

The treatment products having aliphatic chains with twelve carbon atoms are indicated for the treatment of chronic wounds in the detersion phase, for example, patches of necrosis.

The treatment products having aliphatic chains with twenty carbon atoms are indicated for the treatment of chronic wounds in the epidermization phase.

For an acute surgical type wound, for example, the treatment products having aliphatic chains with sixteen carbon atoms and/or aliphatic chains with twelve carbon atoms are particularly indicated because they have biological and bio-adhesion properties making it possible to reduce tissue adherence at interfaces.

Of course, it is possible to attach aliphatic chains of different lengths to polysaccharide macromolecules in order to obtain a product with multiple properties and to increase the efficacy of the product still further.

It will be noted at this point that the document EP-0 341 745 discloses a product obtained by chemical cross-linking, having polysaccharide macromolecules linked to each other by transverse bonds or "cross-linking bridges" consisting of aliphatic chains. Each of these aliphatic chains links two polysaccharide macromolecules by high-energy chemical bonds. This results in the product being in the solid state, or the gel state, and being irreversible.

The aliphatic chains are advantageously attached by a chemical bond.

The said chemical bond can be an ionic bond or a covalent bond, for example, an ester bond.

It is also advantageous for the aliphatic chains attached to a polysaccharide macromolecule to be associated—in the gel state—with aliphatic chains attached to at least one other polysaccharide macromolecule.

The aliphatic chains thus constitute hydrocarbonic arms by means of which the macromolecules are associated with each other.

The invention also relates to a method for producing the wound-treatment system discussed above, during which polysaccharide macromolecules and aliphatic chains each provided with a single attachment group are used and the said polysaccharide macromolecules and the said aliphatic chains are brought into contact so as to attach the aliphatic chains to the macromolecules.

The invention also relates to a natural wound-treatment system such as that defined above, wherein molecules of an active principle are trapped in alveoli of the system in the gel state.

The invention finally relates to a natural wound-treatment system such as that defined above, wherein the living cells are trapped in alveoli of the system in the gel state.

The invention will be better understood with the aid of the following description of different embodiments of the wound-treatment system and of different embodiments of the method for producing the treatment system, with reference to the attached drawing in which:

FIG. 3 illustrates the treatment system in which molecules of an active principle are trapped before the active principle is released;

FIG. 4 illustrates the treatment system of FIG. 3 during the release of the active principle;

FIG. 5 illustrates the treatment system in which living cells are trapped before these cells are released, and FIG. 6 illustrates the treatment system of FIG. 5 during release of the cells.

The wound-treatment system or product comprises polysaccharide macromolecules, 10, 20, 30, in this case alginate macromolecules, and aliphatic chains 11–15, 21–24, 31–33, in this case of the formula $C_nH_{2n-1}$. The number of carbon atoms of the aliphatic chains is in this case 8. In the particular example of the description each aliphatic chain 11–15, 21–24, 31–33 is provided with a single attachment group, in this case an ionised amine group $NH_3^-$, by means of which it is attached to a single alginate macromolecule 10, 20, 30 by a chemical bond consisting of an ionic bond between the ionised amine group $NH_3^-$ and an ionised carboxylate group $COO^-$ of the alginate macromolecule.

Figure 1:
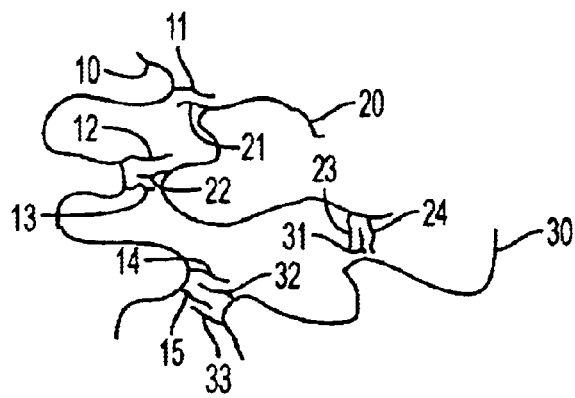
FIG. 1 illustrates three macromolecules of the treatment system in the gel state, according to one particular embodiment.

The aliphatic chains 11–15, 21–24, 31–33 of each macromolecule 10, 20, 30 form hydrocarbonic arms which—when the system is in the gel state—are associated with hydrocarbonic arms of at least one other neighbouring macromolecule. In FIG. 1 it is possible to see that the hydrocarbonic arms of each of the macromolecules 10 (20; 30) are associated with hydrocarbonic arms of the two other macromolecules 20, 30 (10, 30; 10, 20). Each association of hydrocarbonic arms has a number m of hydrocarbonic arms, m being a natural number greater than or equal to two. The hydrocarbonic arms 11/21, 12/22/13, 14/32/15/33, 23/31/24 of each association of arms are linked to each other by physical bonds consisting of hydrophobic interactions. The alginate macromolecules 10, 20, 30 are thus associated with each other by means of their hydrocarbonic arms 11–15, 21–24, 31–33.

The hydrophobic interactions between the associated arms 11/21, 12/22/13, 14/32/15/33, 23/31/24 of the macromolecules 10, 20, 30 have an energy which is both sufficiently great to ensure sufficient strength for the system in the gel state, and sufficiently weak to permit this gel to pass into the solution state under the effect of external forces such as the temperature, mechanical forces, pH, ionic strength, etc. Moreover, this change of state is reversible. In other words, under the effect of external forces, the system can pass from the gel state to the solution state by separation of the associated hydrocarbonic arms 11/21, 12/22/13, 14/32/15/33, 23/31/24 and, conversely, from the solution state to the gel state by association of the hydrocarbonic arms 11–15, 21–24, 31–33.

In this way it is possible, in particular, to pour the alginate system in the solution state onto the wound to be treated so that it conforms to the shape of the wound and comes into close contact with it. After a setting time the system gels and so adheres closely to the wound without the risk of running. Then under the effect of the ionic strength of the biological tissue medium and/or of the pH thereof, the alginate gel located in the proximity of the wound liquefies so that in spite of possible mechanical forces (changes in the wound, movement of the patient) the close contact between the treatment system and the wound will always be maintained.

It would also be possible to attach aliphatic chains to the polysaccharide macromolecules, which aliphatic chains have six, seven or more than eight carbon atoms, in order to obtain a reversible treatment system.

Moreover, one and the same wound-treatment system could have aliphatic chains of different lengths.

In one variation, the aliphatic chains are attached by covalent bonds, in this case ester bonds, as will be explained hereinunder.

Having described the treatment system of the invention, the method for producing this system according to two embodiments will now be described. These two embodiments are the following:
1) attachment of aliphatic chains by covalent bond to alginate macromolecules and
2) attachment of aliphatic chains by ionic bond to alginate macromolecules.

1) Attachment of Aliphatic Chains by Covalent Bond to Alginate Macromolecules

Figure 2:
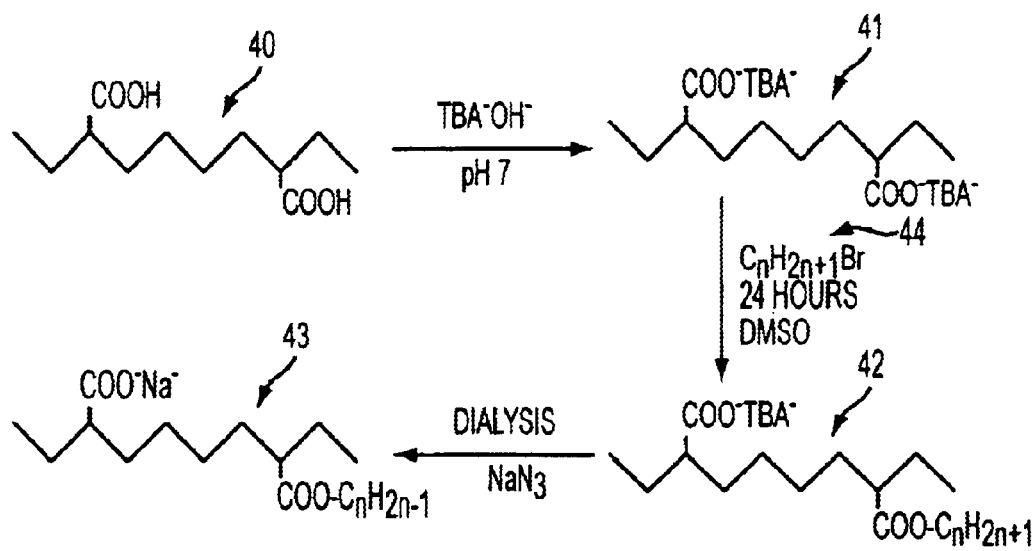
FIG. 2 illustrates stages of the method for producing the treatment system according to one of the embodiments.

With reference to FIG. 2 an aqueous suspension of alginic acid is used at a level of 2% by weight. The suspension includes macromolecules of alginic acid 40 each having a plurality of functional carboxylic groups. These functional groups include, for the most part, a carboxylic group COOH, and in a small proportion of them, a carboxylate group $COO^-$ linked to a sodium ion $Na^-$.

The suspension is neutralised by tetrabutyl ammonium hydroxide ($TBA^-OH^-$) so that the pH is 7. The tetrabutyl ammonium groups $TBA^-$ are substituted for protons of hydrogen $H^-$ in the functional carboxylic groups of the macromolecules of alginic acid 40. The polysaccharide macromolecules 41 thus obtained are those of an ammonium derivative of the alginate including highly reactive functional carboxylic groups ($COO^-TBA^-$).

Then, over a period of 24 hours, the macromolecules 41 are placed in a solvent medium, in this case dimethyl sulfoxide DMSO, in the presence of molecules 44 of an aliphatic brominated derivative of the formula $C_nH_{2n-1}Br$. The number n of carbon atoms of the molecules 44 is twelve. Each molecule 44 has an aliphatic chain (of the formula $C_nH_{2n-1}$) and a bromine atom (Br) forming a single attachment group of the aliphatic chain. Thus the polysaccharide macromolecules 41 are brought into contact with the aliphatic chains 44.

The molecules 44 of the aliphatic brominated derivative react on the macromolecules 41 of the alginate ammonium derivative. Aliphatic chains $C_nH_{2n-1}$ are substituted for the tetrabutyl ammonium groups $TBA^-$ of some of the functional groups of the macromolecules 41 of the alginate derivative, losing their bromine atom. The level of substitution is of the order of 8%. Thus aliphatic chains $C_nH_{2n-1}$ are attached to the alginate macromolecules. Each of these attached aliphatic chains is linked to a carboxylate group ($COO^-$) by a covalent bond, in this case an ester bond. The aliphatic chains are each attached to a single alginate macromolecule. The macromolecules 42 shown in FIG. 2 are obtained.

Finally the solution is dialysed in the presence of sodium azide ($NaN_3$) so as to substitute the remaining tetrabutyl ammonium groups $TBA^-$ of the macromolecules 42 with sodium ions $NA^-$, thus losing the ammonium functionality.

The final reversible alginate system to be used for wound treatment is obtained, including alginate macromolecules 43, illustrated in FIG. 2, each having about 92% of functional sodium carboxylate groups (of formula $COO^-Na^-$) and 8% of functional groups esterified by aliphatic chains with twelve carbon atoms (of formula $COO—C_nH_{2n-1}$).

2) Attachment of Aliphatic Chains by an Ionic Bond to Alginate Macromolecules

Two grammes of sodium alginate are used and placed in suspension in a water-alcohol solution, in this case 140 milliliters of ethanol at 90%.

Molecules of aliphatic amine of the formula $C_nH_{2n-1}NH_2$ are added to the solution. The number n of carbon atoms of the aliphatic amine molecules is in this case 12. Each aliphatic amine molecule has an aliphatic chain (of formula $C_nH_{2n-1}$) and a single amine group (of formula $NH_2$) constituting an attachment group for the aliphatic chain. In solution the amine groups of the aliphatic amine molecules ionise by capturing a proton. Thus the attachment groups of the aliphatic chains are activated by ionisation. Each aliphatic amine molecule thus has a single active attachment group of the formula $NH_3^-$.

In the solution the alginate macromolecules are in contact with the ionised aliphatic amine molecules.

The solution is agitated at ambient temperature for 90 minutes. During this time the ionised aliphatic amine molecules ($C_nH_{2n-1}NH_3^-$) react on the alginate macromolecules and are substituted for the protons of some carboxylic functional groups of the alginate macromolecules. Thus aliphatic chains are attached to the alginate macromolecules by means of their active attachment group $NH_3^-$. The attached aliphatic chains are each linked to a single alginate macromolecule by means of an ionic bond between the attachment group ($NH_3^-$) and a carboxylate group ($COO^-$) of the alginate macromolecule.

The alginate macromolecules thus obtained therefore have carboxylate groups ($COO^-$) some of which are linked to a sodium atom ($Na^-$) by an ionic bond, and some of which are linked to an aliphatic chain ($C_nH_{2n-1}$) by means of an attachment group ($NH_3^-$) by an ionic bond.

Washing is then carried out several times in an ethanol solution, then in a dioxane solution and finally in an acetone solution in order to obtain a dry modified alginate which will provide a reversible alginate gel after dissolution in water.

The use of the treatment system described above for release of an active principle will now be described.

In the treatment system in the gel state (FIG. 3) the alginate macromolecules 51–53 are associated with each other by means of their mutually associated hydrocarbonic arms. By reason of these associations between macromolecules, the gel structure at the macromolecular level is alveolar, the walls of the alveoli being formed by mutually associated hydrocarbonic arms and by skeletal portions of the alginate macromolecule. The alveoli 54–55, or reservoirs, of the system act as traps for other molecules.

In FIG. 3, molecules 60 of an active principle, which are intended to be released at their application site, in other words on the wound to be treated 100, are trapped inside alveoli 54–55.

The molecules 60 of the active principle have been introduced into the treatment system in the solution state. After a setting period in suitable conditions the solution is gelled, trapping the molecules 60 of the active principle in the alveoli 54–55 of the gel.

The treatment gel containing the molecules 60 of the active principle applied to the wound liquefies in the immediate proximity of the skin under the effect of external forces such as body temperature and the ionic strength of the medium. Upon liquefaction the associated arms separate from each other. This means that the alveoli 54–55 open, releasing the molecules 60 of the active principle onto the wound 100.

In one variation (FIG. 4), in place of the active principle, living cells 70, animal or vegetable, are trapped in the alveoli 71, 72 of the reversible treatment gel. These may, for example, be cells intended to re-form damaged cartilage.

In this case the opening of the alveoli 71, 72 for release of the cells 70 could be induced by external forces similar to those discussed above (body temperature, ionic strength, mechanical forces, etc) and/or by internal forces caused by growth of the trapped cells.

What is claimed is:

1. A method for treatment of a necrosis or wound in a subject comprising preparing a wound-treatment product capable of changing state in a reversible manner from a solution state to a gel state and from a gel state to a solution state, the product comprising alginate macromolecules attached to aliphatic chains via ester bonds, wherein each aliphatic chain is attached to a single alginate macromolecule, wherein the aliphatic chains have at least about six carbon atoms and wherein the degree of esterification of the alginate macromolecules is 8%, and applying the wound-treatment product in the solution state to a necrosis or wound of the subject and allowing the wound-treatment product to gel.

2. The method claim 1, wherein the portion of the gelled product proximate to the wound or necrosis is liquefied by the body heat, the ionic strength or pH of the biological tissue of the subject.

3. The method of claim 1, wherein the gel comprises alveoli.

4. The method of claim 3, further comprising trapping at least one active principle within the alveoli.

5. The method of claim 3, further comprising trapping living cells within the alveoli.

* * * * *